United States Patent [19]
Nieh et al.
[11] 4,438,045
[45] Mar. 20, 1984

[54] AMPHOTERIC SURFACTANTS

[75] Inventors: Edward C. Y. Nieh; Carter G. Naylor, both of Austin, Tex.
[73] Assignee: Texaco Inc., White Plains, N.Y.

[21] Appl. No.: 449,957
[22] Filed: Dec. 15, 1982
[51] Int. Cl.[3] .......... C11D 1/88; C07C 101/20
[52] U.S. Cl. .......... 260/501.13; 560/193; 560/196; 560/194
[58] Field of Search .......... 260/501.13; 560/196, 560/193, 194

[56] References Cited

U.S. PATENT DOCUMENTS

| | | | |
|---|---|---|---|
| 3,839,419 | 10/1974 | Samour | 560/193 |
| 3,920,731 | 11/1975 | Naik | 560/196 |
| 4,076,743 | 2/1978 | Matsuda et al. | 562/561 N |
| 4,076,744 | 2/1978 | Kaplan et al. | 562/561 |
| 4,137,191 | 1/1979 | Lohr | 260/501.13 |
| 4,139,553 | 2/1979 | Petzold et al. | 260/501.12 |
| 4,148,762 | 4/1979 | Koch et al. | 260/501.13 |
| 4,180,468 | 12/1959 | Tomidokoro et al. | 424/70 |
| 4,192,817 | 3/1980 | Kaplan et al. | 260/513 N |
| 4,214,102 | 7/1980 | Leenders | 562/564 |
| 4,304,932 | 12/1981 | Phillips et al. | 562/561 |

FOREIGN PATENT DOCUMENTS

| | | | |
|---|---|---|---|
| 554265 | 6/1975 | U.S.S.R. | 260/501.16 |

*Primary Examiner*—Natalie Trousof
*Assistant Examiner*—Raymond K. Covington
*Attorney, Agent, or Firm*—Robert A. Kulason; Jack H. Park; Richard A. Morgan

[57] ABSTRACT

A new composition of matter is revealed.

The composition of matter is the condensation product of succinic anhydride, 3-dimethylamino propylamine or 3-dimethyl aminoethanol and a specified glycidyl ether.

The composition of matter is useful as an amphoteric surfactant.

22 Claims, No Drawings

AMPHOTERIC SURFACTANTS

FIELD OF THE INVENTION

The invention relates to amphoteric surfactants. These surfactants are the condensation products of succinic anhydride, 3-dimethylaminopropylamine or 3-dimethylaminoethanol and a long chain glycidyl ether.

BACKGROUND OF THE INVENTION

Amphoteric surfactants are those which contain both an anionic and a cationic hydrophilic group within the same molecule. Therefore these surfactants have both anionic and cationic functionalities. Typically the cationic portion is a quaternary ammonium derivative while the anionic portion can be a carboxylate, sulfonate or sulfate group.

Prior art listed below describes amphoteric surfactants containing one or more synthetic features of the present invention. Many employ dimethylaminopropylamine, and some use hydrophobic epoxides. Most contain sodium chloride as a co-product.

a. A well-known amphoteric surfactant, generically named cocoamido betaine, is prepared from dimethylaminopropylamine, coconut fatty acid, and sodium chloroacetate:

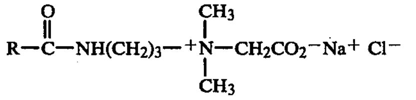

Some trade names for this material are MIRATAINE® (Miranol Chemical Co.), LONZAINE® (Lonza, Inc.), TEGO BETAINE® (Goldschmidt Chemical Corp.) and MONATERIC® (Mona Industries). All contain sodium chloride. One of these betaine products, MIRATAINE CB® was used as a standard lime soap dispersing agent in Examples II-B and IV-B. The lime soap dispersion of the betaine of the present invention in Example I-B was superior and that in Example III-B was slightly inferior to the MIRATAINE®.

b. Other common amphoterics include alkylaminopropionic acids such as DERIPHAT® (Henkel Corp.):

$R—N[(CH_2)_2CO_2H]_2$

Texaco Chemical Company's Experimental Surfactant MA-300 is of this type:

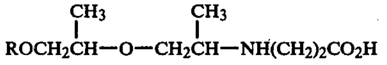

Patents describing other structures include:

| | |
|---|---|
| c. U.S. Pat. Nos. 4,076,743 4,139,553 4,148,762 | 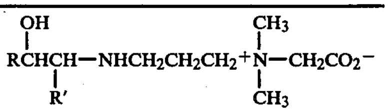 |

These structures are prepared from olefin epoxides and dimethylaminopropylamine. The carboxylate group is introduced by reaction with sodium chloroacetate to form the quaternary ammonium group. Sodium chloride is a co-product of the betaine.

| | |
|---|---|
| d. U.S. Pat. Nos. 4,076,744 4,192,817 | 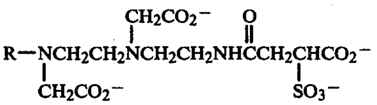 |

This polyanionic surfactant is prepared from N-alkyl diethylenetriamine, maleic anhydride, sodium chloroacetate and sodium sulfite. Since it contains no quaternary ammonium groups, its amphoteric behavior is pH dependent.

| | |
|---|---|
| e. U.S. Pat. No. 4,180,468 | 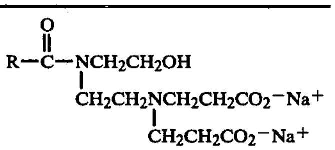 |

This material is made from 1-hydroxyethyl-2-alkylimidazoline, sodium hydroxide and ethyl acrylate. A similar structure is derived from the same imidazoline and alkaline sodium chloroacetate:

| | |
|---|---|
| U.S. Pat. No. 4,304,932 | 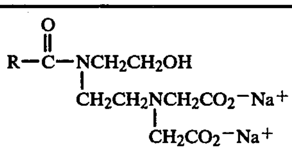 |
| f. U.S. Pat. No. 4,214,102 | 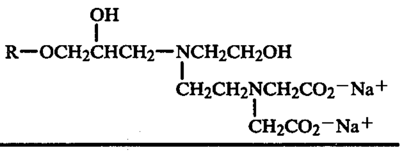 |

Alkyl glycidyl ether, aminoethylethanolamine and sodium chloroacetate are used to prepare this surfactant. Like the structures shown for (b), (d), and (e), this material has no quaternary nitrogen, so its cationic character is apparent only at low pH.

Amphoteric surfactants find utility in a wide number of applications including the textile industry, metal cleaning, industrial cleaning applications, foaming applications as well as cosmetics and health and beauty aides.

SUMMARY OF THE INVENTION

The present invention is a composition of matter of the general formula:

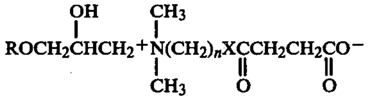

wherein R is a linear or branched alkyl or alkylaryl of from 8 to 20 carbon atoms, X is oxygen or a —NH— radical and n is 2 when X is oxygen and n is 3 when X is —NH—.

These amphoteric surfactants are particularly useful in reducing surface and interfacial tension in aqueous solutions over a wide pH range.

DESCRIPTION OF THE PREFERRED EMBODIMENTS

In one aspect the present invention is a composition of matter of the formula:

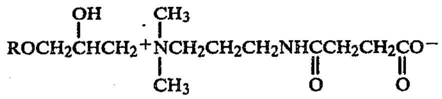

wherein R is selected from a group consisting of a linear or branched alkyl or alkylary radical containing from 8 to 20 carbon atoms. When R is an alkylaryl, R preferably contains from 14 to 20 carbon atoms such as a nonylphenyl or dodecylphenyl group.

Amphoteric surfactants of this configuration are preferably produced in a two step synthesis. In step 1, succinic anhydride is condensed with 3-dimethylaminopropylamine using tetrahydrofuran as solvent. The solid N-3-dimethylaminopropyl hydrogen succinamide product is filtered and dried with characteristically high yields.

In step 2, the N-3-dimethylaminopropyl hydrogen succinamide is dissolved in alcoholic solvent such as methanol, ethanol, isopropanol and the like, along with the desired long chain glycidyl ether. The mixture is heated and digested to produce the desired amphoteric surfactant.

It has been found that surfactants of this configuration are useful in reducing surface and interfacial tension in aqueous media from about 20° C. to 100° C. and over a wide pH range.

In another aspect, the present invention is a composition of matter of the general formula:

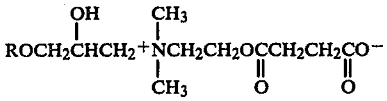

wherein R is a linear or branched alkyl or alkylaryl of 8 to 20 carbon atoms. When R is an alkylaryl, R preferably contains from 14 to 20 carbon atoms such as a nonylphenyl or dodecylphenyl group.

Amphoteric surfactants of this configuration are most conveniently produced in a two step synthesis. In step 1, succinic anhydride is condensed with 3-dimethylaminoethanol in a solvent such as tetrahydrofuran. The solid, crystalline product is collected and dried.

In step 2, the product of step 1 is dissolved in alcoholic solvent such as methanol, ethanol isopropanol and the like, along with the desired long chain glycidyl ether. The mixture is heated and digested to produce the product surfactant, usually with high yield.

The subject compositions do not appear in the prior art.

Reaction of the intermediate tertiary-amine carboxylic acids with hydrophobic epoxides to give surfactant quaternary ammonium carboxylate inner salts (betaines) is unique. The method avoids inorganic salt coproducts.

A functional advantage of amphoteric surfactants of the betaine type is the pH independence of their cationic character. Tertiary-amine surfactants exhibit cationic properties only at low pH where the amine is protonated.

The amphoteric surfactant thereby produced is useful in reducing surface and interfacial tension over a wide pH range.

The present invention also relates to aqueous solution comprising water and from about 0.005 wt% to about 20 wt% or more of a composition of matter characterized by the general formula:

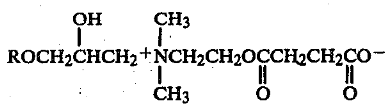

or a monomer characterized by the general formula:

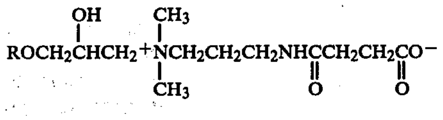

wherein R is selected from a group consisting of a linear or branched alkyl or alkylaryl radical containing from 8 to 20 carbon atoms. When R is an alkylaryl, R preferably contains from 14 to 20 carbon atoms, preferably a nonylphenyl or dodecylphenyl group.

For detergent applications, usually the range of concentration of surfactant in the detergent formulation is between about 1 wt% to about 15 wt% with the residuum being detergent adjuvants described below. In all instances the lower or minimal concentration (0.005% by weight to 0.5% by weight) of surfactant in solution is referred to as an "effective amount" of surfactant. When the surfactants of the present invention are employed as detergents they ordinarily are present in at least the minimal concentrations disclosed accompanied by one or more of the following classes of materials which are generically referred to as detergent adjuvants:

1. Inorganic salts, acids and bases. These are usually referred to as "builders." These salts usually comprise carbonates, hydroxides, phosphates and silicates of the alkali metals as well as their neutral soluble salts. These materials may constitute up to about 99 weight percent of the composition in which they are employed.

2. Organic builders or additives—These are substances which contribute to characteristics such as detergency, foaming power, emulsifying power or soil-suspending effect. Typical organic builders include sodium carboxymethyl cellulose, sequestering agents such as ethylenediaminetetraacetic acid and the fatty monoethanolamides, etc.

3. Special purpose additives—These include solubilizing additives such as lower alcohols, glycols and glycol ethers, bleaches or brighteners of various structures which share in common that they are dyestuffs and they do not absorb or reflect light in the visible range of the spectrum.

The present invention includes a class of amphoteric surfactants with surface active properties over a range of pH values.

The products of the present invention are useful in household detergent products as well as in an enhanced oil recovery process surfactant formulation. For secondary oil recovery processes the solution may additionally comprise brine.

Typical formulations are herein described.

| DETERGENT FORMULATIONS | |
|---|---|
| Parts by wt. | Components |
| A. Drycleaning composition | |
| 10 | Potassium Oleate |
| 13 | Product Example I or III |
| 50 | Dry cleaning solvent |
| 24 | Water |
| 3 | n-Butanol |
| B. Washing Machine Composition | |
| 13 | Product Example I or III |
| 35 | Sodium Tripolyphosphate |
| 30 | Sodium Silicate |
| 20 | Sodium Carbonate |
| 2 | Sodium Carboxymethyl Cellulose |
| C. Automatic Dishwasher Composition | |
| 5 | Product Example I or III |
| 34 | Sodium Silicate |
| 61 | Sodium Tripolyphosphate |
| D. Disinfectant and Detergent Composition | |
| 6.3 | Product Example I or III |
| 45 | Sodium Tripolyphosphate |
| 45 | Sodium Carbonate |
| 3.7 | Oleyl dimethyl ethyl ammonium bromide |

The following Examples illustrate preparation of typical compounds falling within the scope of the invention. It is understood that those Examples are merely illustrative and that the scope of the invention is described in the claims.

EXAMPLE I

I-A. The preparation of N-3-dimethylaminopropyl hydrogen succinamide

A two liter four neck flask equipped with stirrer, thermometer, condenser and addition funnel was charged with succinic anhydride (200 g) and tetrahydrofuran (1400 ml). A homogeneous solution of succinic anhydride in tetrahydrofuran was made when the pot temperature reached 50° C. by heating. Dimethylaminopropylamine was added through the addition funnel at a rate that the exothermic reaction kept the pot temperature at 55° C. to 60° C. without external heating. The reaction mixture was digested at 50° C. for a period of one hour after the addition of the dimethylaninopropylamine was completed. After cooling to ambient temperature the crystalline product was collected on a filter and was dried in a vacuum oven at 40° C. and 3 mm Hg pressure. The yield was 384 g, 96% of the theoretical yield.

I-B. The condensation of N-3-dimethylaminopropyl hydrogen succinamide and glycidyl alkyl ether In a 300 ml three neck flask equipped with stirrer, thermometer and condenser were changed N-3-dimethylaminopropyl hydrogen succinamide (20.0 g), linear alkyl glycidyl ether (20.3 g, equivalent weight 293, Procter and Gamble, Epoxide #8) and isopropyl alcohol (60.0 g). The reaction mixture was heated to 50° C. and digested at 50° C. for a period of five hours. Nonaqueous titration (toluene sulfonic acid in acetic acid) of the reaction product showed 0.89 meq/g of titratable base corresponding to 99% alkylation of tertiary amine salt by alkyl glycidyl ether.

EXAMPLE II

II-A. Aqueous solutions of the amphoteric surfactant 3(3-carboxypropionamido) propyl-3-alkoxy-2-hydroxypropyl dimethyl ammonium inner salt (the product of Example I-B) were prepared. Their surface tension and interfacial tension (water/light mineral oil) were measured at 25° C. Results obtained are summarized below in Table I.

TABLE I

Surface Activity of Aqueous Solutions

| Concentration, wt % | pH[a] | Surface tension dyne/cm | Interfacial tension dyne/cm |
|---|---|---|---|
| 0.5 | 3 | 29.9 | 3.3 |
| 0.5 | 7.6 | 29.2 | 4.4 |
| 0.5 | 11 | 28.2 | 2.5 |
| 0.05 | 3 | 31.6 | 2.4 |
| 0.05 | 7.6 | 29.3 | 4.0 |
| 0.05 | 11 | 25.5 | 2.4 |
| 0.005 | 3 | 37.3 | 5.6 |
| 0.005 | 7.6 | 29.3 | 4.0 |
| 0.005 | 11 | 27.4 | 1.9 |

[a]The solution prepared from the product made in Example I-B and deionized water had a pH of 7.6. Adjustments for higher or lower pH were made by adding a few drops of 0.5N of HCl or NaOH to 100 ml of aqueous solution.

II-B. The amphoteric surfactant of Example I-B was found to be a very effective lime soap dispersant. The method of Bergman and Borghetti (J.A.O.C.S. 1950, 90) was used to compare the lime soap dispersion requirement (LSDR, the amount needed to prevent lime soap coagulation) with the LSDR of a standard amphoteric surfactant:

| | LSDR |
|---|---|
| Product of Examole I-B | 4% |
| MIRATAINE ® CB (cocoamidobetaine) | 8% |

II-C. The product of Example I-B was found to be a strong foaming agent as determined by its Ross-Miles foam test values (0.1% at 120° F.):

140 mm initially at pH 7
128 mm after 5 minutes at pH 7
130 mm initially at pH 10
119 mm after 5 minutes at pH 10

EXAMPLE III

III-A. The Preparation of Dimethylaminoethyl Hydrogen Succinate

In a two liter four neck flask equipped with stirrer, thermometer, condenser and addition funnel were charged succinic anhydride (200 g) and tetrahydrofuran (1400 ml). A homogeneous solution of succinic anhydride in tetrahydrofuran was made when the pot temperature reached 50° C. with external heating. Dimethylaminoethanol (178 g) was added at a rate that the exothermic reaction kept the pot temperature at 55° C. to 60° C. The reaction mixture was digested at 50° C. for a period of two hours after the addition of dimethylaminoethanol was completed. A first crop of crystalline product was collected by filtration and a second crop of product was collected from the mother liquor after concentration to 250 ml by means of reduced pressure distillation. These products were combined and dried in a vacuum over at 40° C. and 3 mm Hg pressure. The total yield was 303 g, 80% of the theoretical yield.

III-B. The Condensation of Dimethylaminoethyl Hydrogen Succinate and Linear Alkyl Glycidyl Ether In a 300 ml three neck flask equipped with stirrer, thermometer and condenser were charged dimethylaminoethyl hydrogen succinate (18.9 g), linear alkyl glycidyl ether (29.3 g), equivalent weight 293, Procter and Gamble Epoxide #8) and isopropyl alcohol (60 g). The reaction mixture was heated to 60° C. and digested at 60° C. for a period of three hours during which solid suspension gradually disappeared.

The essentially complete conversion of the alkyl glycidyl ether was indicated by a clear solution which resulted from mixing one drop of reaction mixture with five milliliters of deionized water. The condensation reaction went to high conversion, was further indicated by a nonaqueous titration (hydrobromic acid in acetic acid) which showed 0.88 meq/g of titratable base in the reaction mixture.

EXAMPLE IV

IV-A. Aqueous solutions of the amphoteric surfactants 2(2-carboxyacetyl)ethyl-3-alkyl-2-hydroxypropyl dimethyl ammonium inner salts are prepared. Their surface tension and interfacial tension (water/light mineral oil) were measured at 25° C. Results are summarized in Table II.

TABLE II

Surface Activity of Aqueous Solutions

| Concentration, wt % | pH[a] | Surface Tension dyne/cm | Interfacial Tension dyne/cm |
|---|---|---|---|
| 0.5 | 3 | 28.6 | 6.5 |
| 0.5 | 7.6 | 28.4 | 5.5 |
| 0.5 | 11 | 27.8 | 4.2 |
| 0.05 | 3 | 25.8 | 4.2 |
| 0.05 | 7.6 | 27.7 | 5.6 |
| 0.05 | 11 | 27.7 | 5.3 |
| 0.005 | 3 | 33.3 | 11.1 |
| 0.005 | 7.6 | 30.2 | 6.6 |
| 0.005 | 11 | 30.9 | 6.3 |

[a]The solution prepared from the product made in Example III and deionized water had a pH of 7.6. Adjustments for higher or lower pH were made by a few drops of dilute HCl or NaOH.

IV-B. The product of Example III was found to be a strongly foaming material by the Ross-Miles test: at 0.1% concentration the initial and 5 minute foam heights were:

139 and 132 mm, respectively, at pH 7.1;

144 and 138 mm, respectively, at pH 10.0.

The product of Example I was a moderately efficient lime soap dispersing agent as measured by the method of Bergman and Borghetti; the lime soap dispersion requirement was about 10.

The principle of the invention and the best mode contemplated for applying that principle have been described. It is to be understood that the foregoing is illustrative only and that other means and techniques can be employed without departing from the true scope of the invention defined in the following claims.

What is claimed is:

1. A composition of matter of the general formula:

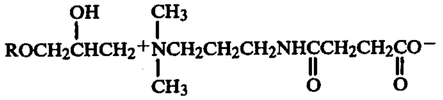

wherein R is selected from the group consisting of a linear alkyl, a branched alkyl and an alkylaryl containing from 8 to 20 carbon atoms.

2. The composition of matter of claim 1 wherein R is an alkylaryl of 14 to 20 carbon atoms.

3. The composition of matter of claim 1 wherein R is nonylphenyl.

4. The composition of matter of claim 1 wherein R is dodecylphenyl.

5. An aqueous solution comprising water and from 0.005 wt.% to 20 wt% of a composition of matter characterized by the general formula:

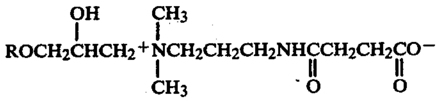

wherein R is selected from a group consisting of a linear alkyl, a branched alkyl and an alkylaryl containing from 8 to 20 carbon atoms.

6. The solution of claim 5 wherein R is an alkylaryl of 14 to 20 carbon atoms.

7. The solution of claim 5 wherein R is nonylphenyl.

8. The solution of claim 5 wherein R is dodecylphenyl.

9. The solution of claim 5 which additionally comprises brine.

10. The solution of claim 5 which comprises from 0.005 wt% to 0.5 wt% of the composition of matter.

11. The solution of claim 5 which comprises from 1 wt% to 15 wt% of the composition of matter.

12. The composition of matter of the general formula:

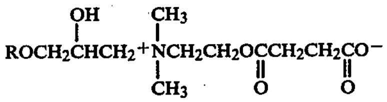

wherein R is selected from the group consisting of a linear alkyl, a branched alkyl and an alkylaryl of 8 to 20 carbon atoms.

13. The composition of matter of claim 12 wherein R is an alkylaryl of 14 to 20 carbon atoms.

14. The composition of matter of claim 12 wherein R is nonylphenyl.

15. The composition of matter of claim 12 wherein R is dodecylphenyl.

16. An aqueous solution comprising water and from 0.005 wt% to 20 wt% of a composition of matter characterized by the general formula:

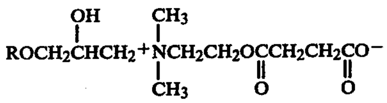

wherein R is selected from a group consisting of a linear alkyl, a branched alkyl and an alkylaryl containing from 8 to 20 carbon atoms.

17. The solution of claim 16 wherein R is an alkylaryl of 14 to 20 carbon atoms.

18. The solution of claim 16 wherein R is nonylphenyl.

19. The solution of claim 16 wherein R is dodecylphenyl.

20. The solution of claim 16 which additionally comprises brine.

21. The solution of claim 16 which comprises from 0.005 wt% to 0.5 wt% of the composition of matter.

22. The solution of claim 16 which comprises from 1 wt% to 15 wt% of the composition of matter.

* * * * *